United States Patent [19]
Duncan et al.

[11] Patent Number: 5,968,517
[45] Date of Patent: Oct. 19, 1999

[54] PROCESS FOR EXTRACTION OF PROANTHOCYANIDINS FROM BOTANICAL MATERIAL

[76] Inventors: Kelvin Winston Duncan, 27b Lodge Place; Ian Alexander Gilmour, 9 Sunvale Terrace, both of Christchurch, New Zealand

[21] Appl. No.: 08/862,170

[22] Filed: May 22, 1997

[30] Foreign Application Priority Data

May 23, 1996 [NZ] New Zealand .............................. 286646

[51] Int. Cl.⁶ .................................................. A01N 65/00
[52] U.S. Cl. ......................................................... 424/195.1
[58] Field of Search ........................................ 424/195.1

[56] References Cited

U.S. PATENT DOCUMENTS

| | | |
|---|---|---|
| 4,211,577 | 7/1980 | Wallin . |
| 4,698,360 | 10/1987 | Masquelier . |
| 4,981,688 | 1/1991 | Ayroles et al. . |
| 5,238,680 | 8/1993 | Connolly . |
| 5,532,012 | 7/1996 | Balentine et al. . |
| 5,607,965 | 3/1997 | Kondo et al. . |

FOREIGN PATENT DOCUMENTS

| | | |
|---|---|---|
| 3976478 | 3/1980 | Australia . |
| 57 75380 | 7/1980 | Australia . |
| 58 99880 | 12/1983 | Australia . |
| 632 67774 | 11/1988 | Japan . |
| 179933 | 2/1976 | New Zealand . |
| 181274 | 6/1976 | New Zealand . |
| 2 34804 | 9/1991 | New Zealand . |
| 9101989 | 2/1991 | WIPO . |

OTHER PUBLICATIONS

Markham et al., "Extractives of Pinus Radiata Bark," *New Zealand Journal of Science*, vol. 16, 1973, pp. 751–761.

Yazaki, "Ultrafiltration of Extracts from Pinus radiata Bark," *Holzforschung*, 37, 1983, pp. 87–90.

Yazaki, "Improved Ultrafiltration of Extracts from Pinus radiata Bark," *Holzforschung*, 39, 1985, pp. 79–83.

Derwent Abstract Accession No. 96–175667/18, Classes B02 C02 JP, A. 08053353 (Taiyo Kagaku KK) Feb. 27, 1996 (Abstract).

Derwent Abstract Accession No. 95–060756/08, Class D13 WO, A. 9501104 (Taiyo Kagaku KK) Jan. 12, 1995 (Abstract).

Derwent Abstract Accession No. 94–173736/21, Classes B02 D13 E13, JP, A. 06116528 (Nikken Food KK) Apr. 26, 1994 (Abstract).

Derwent Abstract Accession No. 89–090844/12, Classes B03 D13 E13 (D21) JP, A. 01042479 (Kikkomann Corp) Feb. 14, 1989 (Abstract).

Derwent Abstract Accession No. 88–357192/50, Class B04 JP, A. 6327774 (Kikkomann Corp) Nov. 4, 1988 (Abstract).

*Primary Examiner*—Herbert J. Lilling
*Attorney, Agent, or Firm*—Greer, Burns & Crain, Ltd.

[57] ABSTRACT

A method for extraction and isolation of proanthocyanidins from biological material. The method includes the steps of hot water extraction of the material after comminution using deoxygenated water, separation of the solids from the liquor, concentration of liquor into a concentrated solution and waste streams, and drying the concentrated solution to a solid product. The hot water can be recycled. The residue results in a usable by-product and the tannins can be extracted from the tannin-rich waste stream. The most preferred biological material is bark from *Pinus radiata* trees which are 15 years old, the bark most optionally coming from the upper portion of the tree.

14 Claims, 2 Drawing Sheets

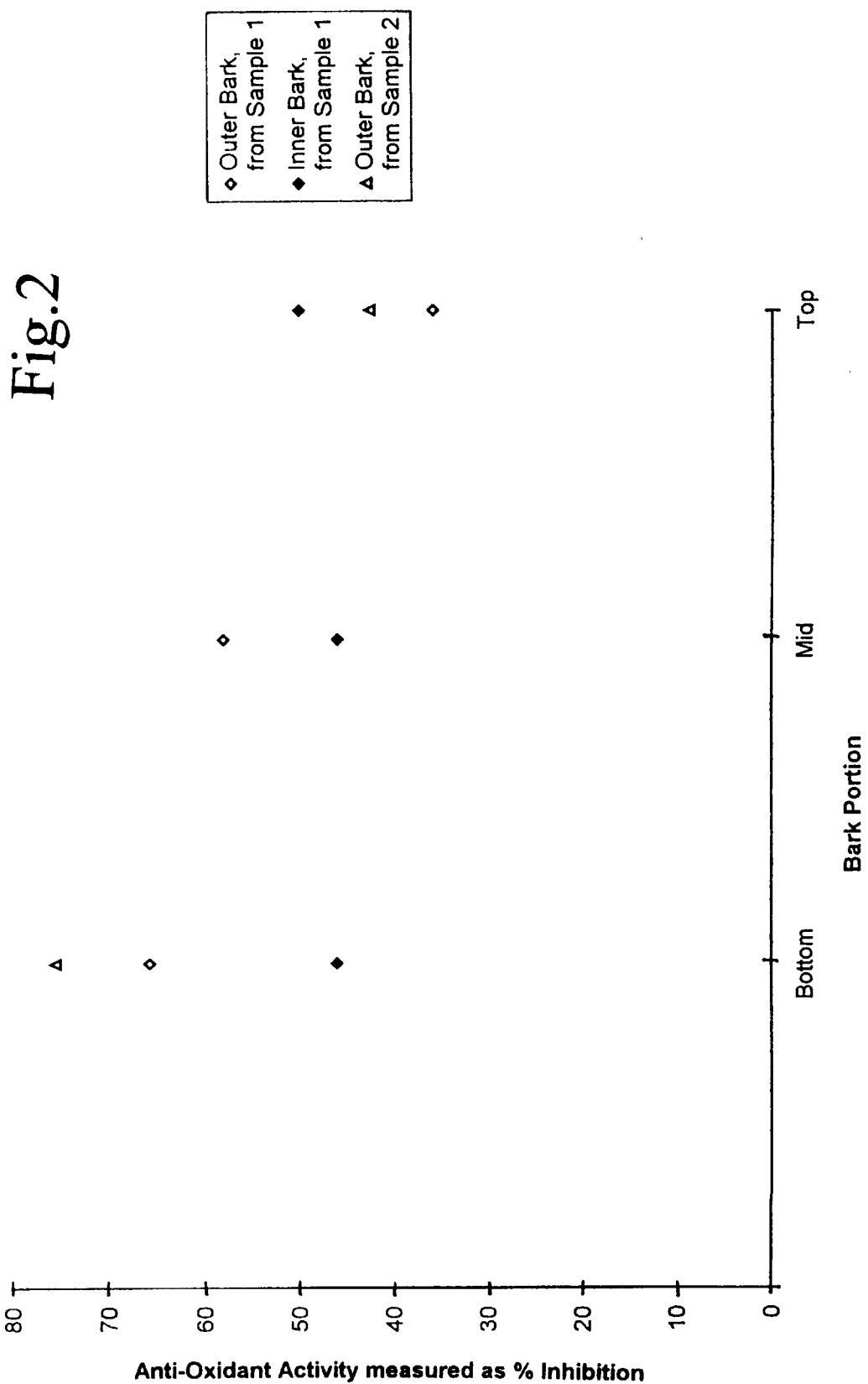

PROCESS FOR EXTRACTION OF PROANTHOCYANIDINS FROM BOTANICAL MATERIAL

FIELD OF THE INVENTION

The present invention relates to a process for the extraction of proanthocyanidins from botanical material, including but not limited to: tree bark, coniferous leaves, grape seeds, grape skins, soya beans, and green tea.

This invention focuses on the extraction of proanthocyanidins from the bark of trees, preferably conifers such as *Pinus radiata*. However, other botanical materials can be substituted for the tree bark in the process described below.

For the purposes of this specification, proanthocyanidins will be referred to as the group of water-soluble, ethyl acetate extractable compounds present in the bark of most trees, but with trees not being the sole source. They are mainly the low molecular weight phenolic monomers, dimers, trimers, oligmers and polymers with reactive hydroxyl groups.

The term "low molecular weight" as used herein means the substance has a molecular weight of 5000 or less. Conversely, the term "higher molecular weight" as used herein means the substance has a molecular weight of greater than 5000.

BACKGROUND OF THE INVENTION
Hot Water Extraction Processes.

The use of hot water extraction of proanthocyanidins from biological material is covered extensively in the prior art. Examples of discussions of such techniques are in the examples below, along with the attendant problems, even if the method claimed in the patent is not solely a hot water extraction technique. Non-bark materials: Japanese Patent Application No. 62101976 (Publication Number 63267774A) reveals that it is possible to obtain a solution of proanthocyanidins derived from the juice of apples, grapes and other fruit, soy beans (etc). U.S. Pat. No. 4,981,688 (Ayroles) discloses extraction of proanthocyanidins from ginko biloba leaves using aqueous ketone solvents. U.S. Pat. No. 5,607,965 (Kando) discloses extraction from a grape extract. U.S. Pat. No. 5,532,012 (Balentine) discloses an extractive from tea. Tree bark materials: The most common bark discussed is that of *Pinus radiata* bark. However other species of bark or tree have been used for extraction of proanthocyanidins. For example: Australian AU B 58998/80 uses Croton or a Calophyllum species as the starting material and the acacia species is used in NZ Patent No. 181274 (NZ Forest Products).

The extractives of *Pinus radiata* bark (both inner and outer) have been well documented. For example, Markham and Porter in New Zealand Journal of Science (1973, Vol 16, p. 751) detail the phenolic compounds which can be extracted with ethyl acetate solution, amongst others. These include procyanidins, high molecular weight condensed tannins and phenolic acid compounds.

A range of methods of hot water extraction of *Pinus radiata* have been proposed: Yazaki (Holzforschung 37 (1983) 87) reviewed hot water extraction of bark, followed by freeze drying, and dissolution in 10% aqueous sodium hydroxide solution. This was then subjected to micro-filtration and ultra-filtration. However, uniform quality of the extract was noted as a problem.

This process is similar to that disclosed in Australian Patent Application No. 57753/80 (CSIRO). Yazaki (Holzforschung 39 (1985) 79) reviewed the results of a similar process, using solvent solutions which obtained more reliable results. NZ Patent No. 179933 (NZ Forest Products) also noted the problem of uniformity of extract. In NZ Patent No. 234804 (Chem Eng Contracts) there is extensive discussion of the problems relating to hot water extraction processes. In NZ Patent No. 181274 hot water extraction is disclosed, but with a two stage control of the pH value of the extractive solution.

Another problem that has been noted with extraction processes of proanthocyanidins is that in some techniques there is degradation of the product as the proanthocyanidins starts reacting before the extraction process is completed. This is countered by control of the pH (for example: NZ Patent No. 181274, NZ Forest Products Ltd) or control by selection of solvent(s) used (for example, Yazaki 1985).

In summary, there are three problems relating to hot water extraction processes. Firstly, when only hot water extraction alone is used, high purity yield has been found to be too low for viability of the process commercially. Low yields are also noted from the yields disclosed in Japanese Patent Application No. 62101976 (Publication Number 63267774A). This patent discloses that it is possible to obtain a solution of high purity and yield by the treatment of a proanthocyanidin-containing solution (in 0.5% v/v alcohol) with ultra-filtration and/or reverse osmosis. However the yield disclosed in the examples given is 0.72% w/w or less of proanthocyanidins.

Second and thirdly, uniformity of quality is sometimes problematic. This may result from the selection of the size or type of material for the extraction process or from the proanthocyanidins reacting with chemicals present in the process and thus resulting in a degraded or less pure product.

An object of the present invention is the provision of a method of extraction for proanthocyanidins which overcomes the disadvantages of the known processes of purely hot water extraction and still produces a commercially acceptable yield of high purity of the proanthocyanidins. This object includes the avoidance of solvents other than water, and avoids the use of other chemical additives such as sodium hydroxide and sodium chloride for pH adjustment and salting down.

SUMMARY OF THE INVENTION

The present invention provides a method for extraction and isolation of proanthocyanidins from botanical material, said method including the steps of:

reducing the material product to particles of a size less than 15 mm;

extraction of the material in hot water in a reaction vessel wherein said hot water is deoxygenated hot water, said extraction continuing for between 1 minute and 20 hours;

separation to leave a residue and a liquor;

partitioning the liquor by a method selected from: ultra-filtration; reverse osmosis; and a combination of the two in series; which partitioning results in concentrated solutions; and waste streams;

drying the concentrated solutions to yield a solid product of proanthocyanidins; and separating the waste streams into water and a tannin rich fraction from which the tannins are recovered by ultra-filtration.

Preferably said botanical material is tree bark; more preferably *Pinus radiata* bark.

More preferably, the bark is selected from the upper portion (top or middle part) of trees which are between 8 and 20 years old, most preferably 15 years old. The material is preferably a mixture of inner and outer bark. Such material is readily available in some forests where slightly immature trees are felled for the use of the lower half of the tree for poles, posts (etc). In such use the top half of the tree is not otherwise commercially usable, yet the bark is easily removed in known commercial debarking operations. The bark can be green or seasoned.

Preferably, the drying method used is vacuum, spray or freeze drying.

Preferably the (spent bark) residue, being free from volatiles and tannins, is a usable by-product of the process.

Preferably the hot water is deoxygenated by boiling. Preferably the water used in the above extraction step is recycled.

BRIEF DESCRIPTION OF THE DRAWINGS

By way of example only, a preferred embodiment of the present invention is described in detail with reference to the accompanying drawings and with reference to *Pinus radiata* tree bark.

FIG. 2 is a graph of the anti-oxidant activity of the resultant product for bark from different parts of a tree.

DETAILED DESCRIPTION OF THE INVENTION

Figure 1:
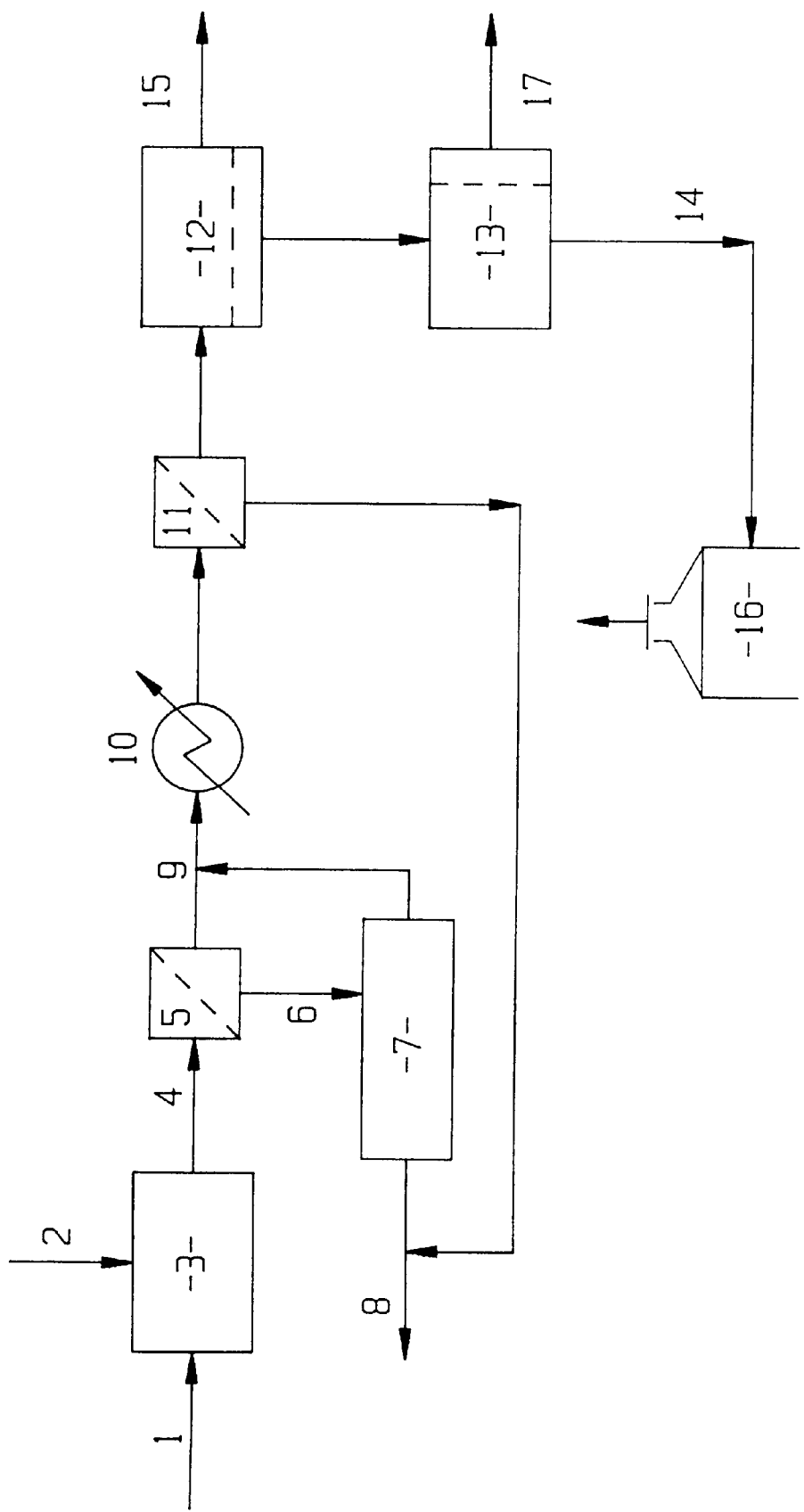
FIG. 1 is a diagrammatic representation of a batch process of the present invention.

Referring to FIG.1 , screened bark is processed by known means (for example: a hammer mill, a knife mill or a mulcher) to increase the surface area of bark 1. The screening is to remove stones, rocks and other extraneous matter. The bark may be fresh, wet or dry, and may be inner bark (cork with phellogen and some phelloderm) or outer bark (crushed epidermal cells) or a combination thereof. The bark 1 is preferably produced from screened bark. However, the size of wet bark is preferably of uniform size initially. The particles of bark 1 produced are preferably 15 mm and more preferably smaller than this.

The resultant stream of bark 1 is added to previously boiled water 2 in a reaction vessel 3. The preferred extraction process is a batch operation, either with or without agitation. Alternatively a series of continuous stirred reactors or a plug flow continuous reactor may be used to accomplish the hot water extraction. The advantage of the batch process is that there may be any time interval desired between stages once the solids are removed from the hot water 2.

In the case where continuous extraction in a series of one or more continuous stirred reactors or plug flow continuous reactors occurs, in practice it has been found that the extraction time can be reduced to between one to 10 minutes.

Referring back to FIG. 1, any ratio of water 2 to bark 1 can be used. Preferably, the ratio is seven liters of water to a kilogram of bark 1. The mixture is heated, in a batch operation, in the vessel 3 for a period of between 20 minutes to 20 hours, more preferably 30 minutes. The temperature in the reaction vessel 3 is between 60 and 100° C. at atmospheric pressure. Alternatively, if the reaction is conducted at an elevated pressure, the temperature in the reaction vessel 3 is between 100 and 125° C.

The extraction time may vary. However in practice it has been found that 30 minutes of reaction produces an optimum yield.

The vessel 3 can be heated indirectly with steam by means of an internal coil or external jacket. Direct heating of the contents may also be used by injecting live steam into the vessel. The hot water extraction step may also be carried out under pressure up to a temperature of 125° C.

A resultant liquor stream 4 is separated by a physical separation process in a chamber 5 to produce a bark residue 6 and filtrate 9. This process may be any one of the following: centrifuging; decanting; filtering; or a combination thereof.

The bark residue 6 is further pressed (stage 7) to remove excess liquor and is returned to the filtrate 9 from the chamber 5. The pressed residue 8 is then further processed by known method (not shown; for example—dried in an oven and/or compressed into bales or pellets) for use as a by-product (for example as a plant growth medium or fuel).

The filtrate 9 is cooled to a temperature between 25° to 30° C. in a heat exchanger 10. The water used in this step may be the water 2 passed to the reaction vessel 3. The filtrate 9 is further filtered by passage through a microporous filter 11 which removes substantially all suspended solids above 1 µm in size. The separated solids may be combined with the pressed residue 8 for processing as hereinbefore described.

The filtrate 9 then passes through one of the following three options: an ultra-filtration step 12; a reverse osmosis step 13; or a combination of each of these steps. FIG. 1 shows the last of these options (13,12). The result of this stage of the process is to fractionate the dissolved components in the filtrate 9 by molecular size and shape, into separate streams (14, 15, 17).

Both the reverse osmosis unit and the ultra-filtration unit (13, 12) are fitted with membranes with micropores sized according to a pre-determined cut-off in molecular size in the streams 15, 17. The pre-determined molecular size is in the range 1000 to 5000 Daltons, but may vary further, if so desired.

The membranes of the reverse osmosis unit and the ultra-filtration unit (13, 12) may be operated under different modes such as steady flow, or pulsating flow in order to increase the flux rates. The temperature of the filtrate 9 through the separation stages may range from ambient to 100° C., depending on membrane operating conditions. Operation pressures can be altered to adjust flux rates as required within membrane specifications.

The desired proanthocyanidins, along with similar sized dissolved compounds, pass through to a concentrated solution 14. The proanthocyanidins are recovered from the concentrated solution 14 by removing the water by one of a range of methods in a vessel 16. Said method is selected from the group: evaporation; crystallisation; freeze drying; vacuum drying; and a combination thereof. In a small scale process it has been found that freeze-drying is the optimal method. However on a large scale process the recovery method is preferably reverse osmosis followed by drying. A membrane with a concentration factor of between 2–5 (as a minimum) is most preferable. The resultant product is brown coloured crystalline flakes which contain all the desired proanthocyanidins.

The following compounds have been found to collect in the concentrated solution 14 and include a range of flavonoids and other low molecular weight phenolic compounds: (+)-Catechin, (+)-Gallocatechin, (+)-Dihydroquercetin (Taxifolin), Quercetin, Myricetin, 3,5-Dihydroxystilbene (Pinosylvin), 3,5,3',4'-Tetrahydroxystilbene (Astringenin), 3,5,3',4'-

Tetrahydroxystilbene-4'-β-glucoside (Astringenin-4'-β-glucoside) and Procyanidins B1, B3, B6 and C2.

The resultant product has been established as having the same anti-oxidant activity (free radical scavenging) as commercially available pure pine bark extract samples. The assay used to establish anti-oxidant activity was as described in Test 1 below.

It has been found that some non-phenolic compounds remain in the resultant product. These can be removed by further physical purification of the product, if so desired.

The stream 15 includes the higher molecular weight compounds which include natural tannins. If so desired, the stream 15 can be subjected to further processing and cleaning to remove the water and recover the tannin in solid form (not shown). The resultant water (along with the stream 17) can also be further purified (if so desired) for safe discharge or for reuse in the reaction vessel 3.

In practice, yields between 0.5 to 10.0% by weight of proanthocyanidins have been obtained based on oven dried bark weight, (depending on the quality and age of the bark). The most common yield has been found to be between 6.5% and 9.6% by weight when using bark from Pinus radiata trees from the top and middle portion of trees of approximately 15 years of age.

Referring to FIG. 2 this graph shows the results of the anti-oxidant activity of the resultant product as a percentage of the anti-oxidant inhibition, when bark is selected from different parts of Pinus radiata trees. The figures produced are from a samples resulting from a 9 hour extraction time. The trees were approximately 15 years old and from a commercial forestry operation in the North Island of New Zealand.

The assays were conducted in accordance with the testing procedure outlined below. In each assay 1 mg/L of each bark sample was added to the reaction mixture. The decrease in the rate of lipid oxidation that the test samples caused is shown as a percentage of the control mixture where no inhibitor anti-oxidants were added. One hundred percent inhibition indicates that the anti-oxidant at the stated concentration was able to completely stop the chain reaction.

The inhibitors were made up by dissolving the resultant product to a concentration of 1 mg/mL with 50% methanol and then further diluting to 50 μg/mL and 20 μL of this was added to 1 mL of the peroxidation mixture to give a final concentration of 1 μg/mL.

Thus for this process the bark from any part of the tree produces an antioxidant of an acceptable standard, and indicates that the bark from the top and upper part of the tree can be equally advantageous. As such bark is more readily available commercially, the process does not suffer from using such bark alone.

TESTING

1. Peroxide Radical Scavenging Antioxidant Assay.

This assay measured the ability of the product to inhibit oxidation of a linoleic acid suspension by the free radical generated compound AAPH (Journal of Organic Chemistry (1993), Vol 58, 3521–32).

One mg/l of the resultant product was added to the reaction mixture. A comparative test was also done using commercially available pure pine bark extract samples. The decrease in the rate of lipid oxidation is shown below as a percentage of the control mixture where no inhibitor anti-oxidants were added. One hundred percent inhibition indicates that the antioxidant at the stated concentration was able to completely stop the chain reaction.

Resultant product: 70–79% inhibition depending on sample tested

Sample(1) 70% inhibition (1) Source: commercially available pure pine bark extract, purchased as pure proanthocyanidin from M.W. International Ltd in the USA. The source of the tested resultant product samples was Pinus radiata trees between the age of 8 to 20 years, from the North Island of New Zealand.

2. Toxicity Tests.

Toxicity tests (acute and chronic) of the resultant product have been conducted on mice.

Acute: Fifteen animals from a standard commercial strain were divided into 3 groups, one of which was used as the control group. A second group was administered dosages for 24 hours of the product adjusted from human dosage on a weight basis. The third group was dosed with 100 times the level of dose administered to the second group, for 24 hours. Results: No adverse reactions or effects were observed in either group 2 or group 3.

Chronic: The above acute dosage levels were continued in the same groups of mice for five months.

Results: A noticeable change in the social habits of the third group was observed. The group was less active, but more social and more curious than the control group. Increases in weight were observed, leading to a tentative conclusion of the positive effect on metabolic performance. No adverse reactions or effects were observed in either group 2 or group 3. On stopping the chronic dosage in group 3, there was a decrease in the average level of activity, and body mass; but food consumption remained substantially unchanged.

The tests show no toxicity (acute or chronic) of the resultant product for mice.

We claim:

1. A method for extraction and isolation of proanthocyanidins from botanical material, said method including the steps of:

reducing the material product to particles of a size less than 15 mm;

deoxygenating a supply of water through heating said water to 100° C. to provide deoxygenated water;

adding said material to the deoxygenated water;

extracting said material in said deoxygenated water in a reaction vessel, said extraction continuing for between one minute and 20 hours at a temperature between 60 and 100° at atmospheric pressure, wherein said extraction media contains only water;

separating said material in said vessel to leave a residue and a liquor;

partitioning the liquor by a method selected from the group consisting of ultra-filtration, reverse osmosis and a combination of the two in series, which partitioning results in concentrated solutions and waste streams; and drying the concentrated solutions to yield a solid product of proantdocyanidins using one of freeze drying and vacuum drying;

wherein said method utilizes only water as a solvent; and wherein the solid product comprises(+)-Catechin (+)-Gallocatechin, (+)-Dihydroquercetin (Taxifolin), Quercetin, Myricetin, 3,5-Dihydroxystibene, 3,5,3',4'-Tetrahydroxystilbene, 3,5,3',4'-Tetrahydroxystilbene-4-β-glucoside and Procyamdins B1, B3, B6 and C2.

2. A method for extraction and isolation of proanthocyanidins as claimed in claim 1 wherein the temperature of the hot water is between 100° and 125° C. at pressures above atmospheric pressure.

3. A method for extraction and isolation of proanthocyanidins as claimed in claim 1 wherein the reaction vessel is heated by a method selected from: direct beating from an internal coil; indirect heating from an external jacket; live steam injection in the vessel; and a combination of any of these.

4. A method for extraction and isolation of promthocyanidins as claimed in claim 1 wherein the method of extraction is a batch process.

5. A method for extraction and isolation of proanthocyanidins as claimed in claim 1 wherein the extraction is conducted in a series of one or more continuous stirred reaction vessels for a time between one and 10 minutes.

6. A method for extraction and isolation of proanthocyanidins as claimed in claim 1 wherein the extraction is conducted in a series of one or more plug flow continuous reaction vessels for a time between one and 10 minutes.

7. A method for extraction and isolation of proanthocyanidins as claimed in claim 1 wherein the biological material is selected from: inner *Pinus radiata* bark (cork with phellogen and some phelloderm); outer (crushed epidermal cells) *Pinus radiata* bark; and a combination thereof.

8. A method for extraction and isolation of proanthocyanidins as claimed in claim 7 herein said bark is selected from trees the age of which is in the range 8 to 20 years.

9. A method for extraction and isolation of proanthocyanidins as claimed in claim 8 wherein the age of the tree is 15 years.

10. A method for extraction and isolation of proanthocyanidins as claimed in claim 7 wherein the bark is selected from the middle and upper part of the tree.

11. A solid product containing proanthocyanidins produced by the method for extraction and isolation of proanthocyanidins from botanical material as claimed in claim 1.

12. A tannin-rich solution produced by the method for extraction and isolation of proanlthocyandins from botanical material as claimed in claim 1.

13. A solid by-product resulting from the combination of and drying of the liquor and waste streams from the method for extraction and isolation of proanthocyanidins from botanical material as claimed in claim 1.

14. A method for extraction and isolation of proanthocyanidins as claimed in claim 3 wherein the method of extraction is a batch process.

\* \* \* \* \*